US007458962B2

(12) United States Patent
McWethy et al.

(10) Patent No.: US 7,458,962 B2
(45) **Date of Patent: *Dec. 2, 2008**

(54) RETRACTABLE NEEDLE MEDICAL DEVICE FOR INJECTING FLUID FROM A PRE-FILLED CARTRIDGE

(75) Inventors: Robert T. McWethy, Ventura, CA (US); John Barker, Ventura, CA (US); Michael J. Botich, Oxnard, CA (US); Thor R. Halseth, Simi Valley, CA (US)

(73) Assignee: MDC Investment Holdings, Inc., Wilmington, DE (US)

( * ) Notice: Subject to any disclaimer, the term of this patent is extended or adjusted under 35 U.S.C. 154(b) by 644 days.

This patent is subject to a terminal disclaimer.

(21) Appl. No.: 10/863,185

(22) Filed: Jun. 8, 2004

(65) Prior Publication Data

US 2004/0249358 A1 Dec. 9, 2004

Related U.S. Application Data

(63) Continuation of application No. 09/916,180, filed on Jul. 26, 2001, now Pat. No. 6,752,798.

(60) Provisional application No. 60/221,305, filed on Jul. 28, 2000, provisional application No. 60/276,407, filed on Mar. 15, 2001.

(51) Int. Cl.
*A61M 31/00* (2006.01)

(52) U.S. Cl. ....................... 604/506; 604/110; 604/194; 604/196; 604/198; 604/201; 604/227; 604/232; 222/327; 433/89

(58) Field of Classification Search ................. 604/110, 604/500, 506, 181, 187, 194–199, 201, 208–210, 604/220, 224, 232, 227–229, 234, 235, 240–244, 604/263; 222/325–327, 386, 328; 433/80, 433/87–90, 98; 128/919
See application file for complete search history.

(56) References Cited

U.S. PATENT DOCUMENTS

| | | | |
|---|---|---|---|
| 3,306,290 | A | 2/1967 | Weltman |
| 4,585,445 | A | 4/1986 | Hadtke |
| 4,655,751 | A | 4/1987 | Harbaugh |
| 4,675,005 | A | 6/1987 | DeLuccia |
| 4,723,943 | A | 2/1988 | Spencer |
| 4,731,068 | A | 3/1988 | Hesse |
| 4,737,144 | A | 4/1988 | Choksi |
| 4,738,663 | A | 4/1988 | Bogan |

(Continued)

*Primary Examiner*—Nicholas D. Lucchesi
*Assistant Examiner*—Quynh-Nhu H Vu
(74) *Attorney, Agent, or Firm*—Stoel Rives LLP

(57) ABSTRACT

A device for injecting fluid from a pre-filled cartridge is provided. The device includes a needle for piercing a patient. After an injection, the needle can be retracted to prevent inadvertent contact with the contaminated needle. A needle retainer releasably retains the needle in the retracted position. The needle can subsequently be re-extended to administer a subsequent injection. After the cartridge is emptied, the cartridge can be removed, if desired, and replaced with another cartridge for additional injections. Alternatively, the needle can be substantially permanently retracted into the device and safely disposed of in a sharps container.

19 Claims, 8 Drawing Sheets

10 22 20 25 24 32 33 37 46 64 29 42 44 21 50 55 27 34 26 35 30 60 40

U.S. PATENT DOCUMENTS

| | | | | |
|---|---|---|---|---|
| 4,744,790 | A | | 5/1988 | Jankowski et al. |
| 4,744,791 | A | | 5/1988 | Egolf |
| 4,767,413 | A | | 8/1988 | Haber et al. |
| 4,804,372 | A | | 2/1989 | Laico et al. |
| 4,820,275 | A | | 4/1989 | Haber et al. |
| 4,826,489 | A | | 5/1989 | Haber et al. |
| 4,834,717 | A | | 5/1989 | Haber et al. |
| 4,919,657 | A | | 4/1990 | Haber et al. |
| 4,931,040 | A | | 6/1990 | Haber et al. |
| 4,935,014 | A | | 6/1990 | Haber |
| 4,946,441 | A | | 8/1990 | Laderoute |
| 4,988,339 | A | | 1/1991 | Vadher |
| 5,067,945 | A | | 11/1991 | Ryan et al. |
| 5,078,698 | A | | 1/1992 | Stiehl et al. |
| 5,098,382 | A | | 3/1992 | Haber et al. |
| 5,106,379 | A | | 4/1992 | Leap |
| 5,112,307 | A | | 5/1992 | Haber et al. |
| 5,167,632 | A | | 12/1992 | Eid et al. |
| 5,167,641 | A | | 12/1992 | Schmitz |
| 5,201,708 | A | | 4/1993 | Martin |
| 5,201,719 | A | | 4/1993 | Collins et al. |
| 5,261,880 | A | | 11/1993 | Streck et al. |
| 5,269,766 | A | | 12/1993 | Haber et al. |
| 5,306,258 | A | | 4/1994 | De La Fuente |
| 5,330,440 | A | | 7/1994 | Stanners et al. |
| 5,336,200 | A | | 8/1994 | Streck et al. |
| 5,346,480 | A | | 9/1994 | Hess et al. |
| 5,350,367 | A | | 9/1994 | Stiehl et al. |
| 5,358,491 | A | | 10/1994 | Johnson et al. |
| 5,360,408 | A | | 11/1994 | Vaillancourt |
| 5,368,568 | A | | 11/1994 | Pitts et al. |
| 5,405,326 | A | | 4/1995 | Haber et al. |
| 5,429,611 | A | | 7/1995 | Rait |
| 5,445,620 | A | | 8/1995 | Haber et al. |
| 5,514,107 | A | | 5/1996 | Haber et al. |
| 5,531,706 | A | | 7/1996 | de la Fuente |
| 5,573,513 | A | * | 11/1996 | Wozencroft ................. 604/198 |
| 5,709,662 | A | | 1/1998 | Olive et al. |
| 5,891,104 | A | | 4/1999 | Shonfeld et al. |
| 5,997,512 | A | | 12/1999 | Shaw |
| 5,997,513 | A | | 12/1999 | Smith et al. |
| 6,036,675 | A | | 3/2000 | Thorne et al. |
| 6,077,244 | A | * | 6/2000 | Botich et al. ................ 604/110 |
| 6,752,798 | B2 | * | 6/2004 | McWethy et al. ........... 604/506 |
| 7,033,343 | B2 | * | 4/2006 | McWethy et al. ........... 604/506 |
| 2001/0004970 | A1 | | 6/2001 | Hollister et al. |

* cited by examiner 194
180
190
184
185
182
192
160
201
154
140
146
152
151
128
126
130
200
122
124
120
110

RETRACTABLE NEEDLE MEDICAL DEVICE FOR INJECTING FLUID FROM A PRE-FILLED CARTRIDGE

RELATED APPLICATIONS

This application is a continuation of U.S. application Ser. No. 09/916,180, filed Jul. 26, 2001, which is set to issue on Jun. 22, 2004 as U.S. Pat. No. 6,752,798, which claims priority under 35 U.S.C. §119 to U.S. Provisional Application No. 60/276,407, filed Mar. 15, 2001 and U.S. Provisional Application No. 60/221,305, filed Jul. 28, 2000. Each of the foregoing applications is hereby incorporated herein by reference.

FIELD OF THE INVENTION

The present invention relates to needle-bearing medical devices having a retractable needle for injecting fluid into a patient. More specifically, the present invention relates to such a device configured for injecting fluid from a pre-filled cartridge. Preferably, the needle is selectively retractable and re-extendable during use to allow the contaminated needle to be shielded between successive needle injections. In one embodiment of the invention, the needle is permanently retractable after use so that the contaminated needle is shielded to prevent inadvertent contact with the sharpened tip of the needle.

BACKGROUND

Various types of medical devices employ a needle for piercing the skin of a patient for diagnostic or therapeutic purposes. One such device is a device for introducing medicine from a pre-filled cartridge into a patient. Handling of such medical devices after the needle is withdrawn from the patient can result in transmission of various pathogens, most notably human immunodeficiency virus (HIV), due to an inadvertent needle stick to medical personnel.

Several devices are known that allow fluid to be injected into a patient from a pre-filled cartridge. For instance, in dental practice, a cartridge injector is used for injecting novocaine into a patient. These cartridge injectors are normally made with metal, that may be chrome or nickel plated and are intended to be sterilized by an autoclave after use.

When using a dental injector, it is common to administer several small doses of novocaine. After the first injection, the needle is considered contaminated, and current practice, as outlined by OSHA guidelines, requires recapping the needle. Although recapping by hand is prohibited by OSHA guidelines, some dentists still practice this unsafe technique, which can lead to an inadvertent needle stick. One recommended technique for safely recapping the needle uses a cap holder, mounted to the dental tray being used. Although safer than recapping the needle by hand, using a cap holder still exposes the contaminated needle when the device is moved from the patient's mouth to the cap holder for recapping. Another problem with recapping is that if the dentist is not careful when centering the needle into the cap, the needle tip can scrape the sidewall of the cap. If this happens, the needle can be dulled or can scrape off small pieces of plastic that could be injected into the patient during subsequent injections.

SUMMARY OF THE INVENTION

In light of the foregoing, a medical device is provided that allows a series of injections to be made to a patient. Between each injection, the contaminated needle is shielded against inadvertent contact. After use, the needle is shielded to prevent inadvertent contact with the contaminated needle during subsequent handling of the used device.

More specifically, the present invention provides a medical device having a hollow housing for receiving a pre-filled cartridge and a plunger for expelling fluid from the cartridge. A needle having a sharpened tip projects forwardly from the forward end of the housing. A biasing element, such as a spring, is operable to displace the needle rearwardly. A first lock releasably locks the needle in a projecting position in which the sharpened tip of the needle is exposed for use. A second lock releasably retains the needle in a shielded position in which the sharpened tip of the needle is shielded against inadvertent contact. In one embodiment of the invention, a third lock fixedly retains the needle in a second shielded position in which the sharpened tip of the needle is shielded against inadvertent contact, and the needle is substantially permanently retained against further axial displacement.

The present invention also provides methods for safely providing a plurality of injections to a patient from a medical device having a needle with a sharpened tip operable between a projecting position, in which the needle is exposed for use, and a retracted position, in which the needle is shielded against inadvertent contact. According to the method, the patient is pierced with the sharpened tip of the needle, and fluid contained in a cartridge is injected into the patient. The needle is then retracted to a first retracted position so that the sharpened needle tip is shielded against inadvertent contact. The needle is releasably locked in the first retracted position by a first lock. The needle is then re-extended into the projecting position, the patient is pierced a second time, and fluid is injected into the patient a second time. In one method, the cartridge can be removed and a new cartridge inserted to provide additional medication for further injections. In another method, the needle can be permanently locked into a second retracted position so that the sharpened needle tip is shielded against inadvertent contact.

DESCRIPTION OF THE DRAWINGS

The foregoing summary as well as the detailed description below will be better understood when read in conjunction with the drawings, in which.

DETAILED DESCRIPTION OF THE PREFERRED EMBODIMENTS

Figure 1:
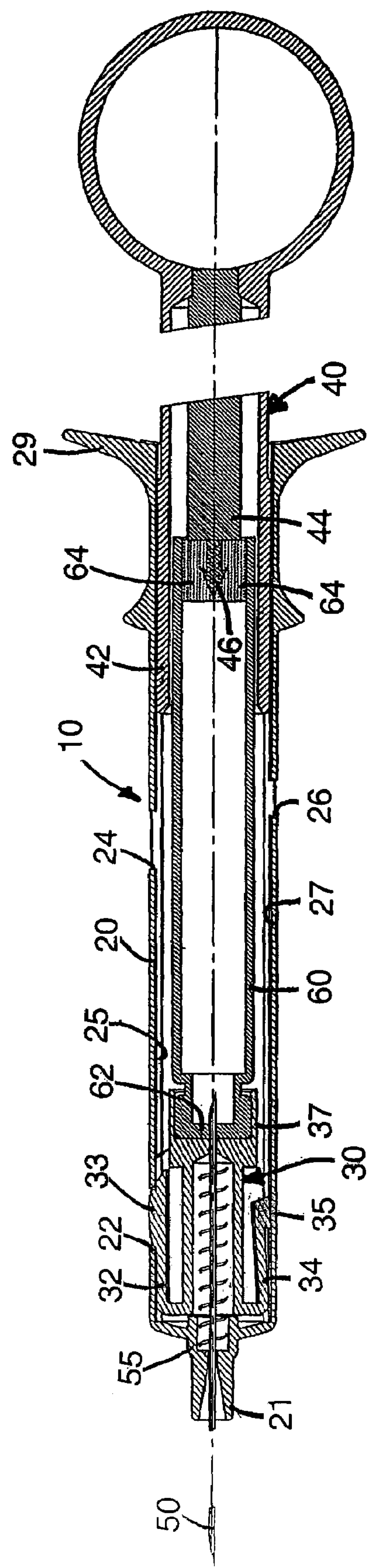
FIG. 1 is a cross-sectional view of a retractable needle medical device for injecting fluid, manifesting aspects of the present invention, illustrating the device in a ready for use position.
Figure 2:
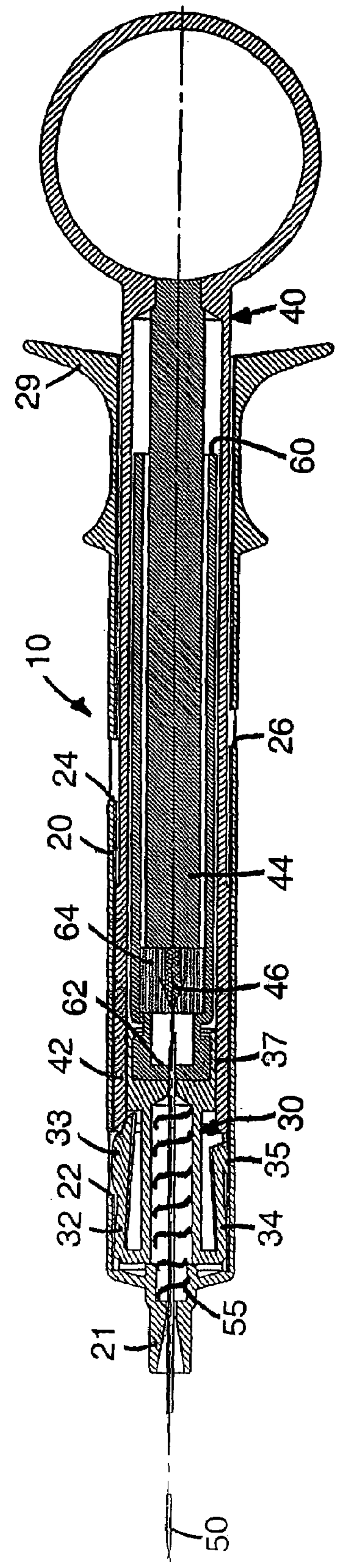
FIG. 2 is a cross-sectional view of the device illustrated in FIG. 1, illustrating the device in a position in which all of the fluid has been expelled.
Figure 3:
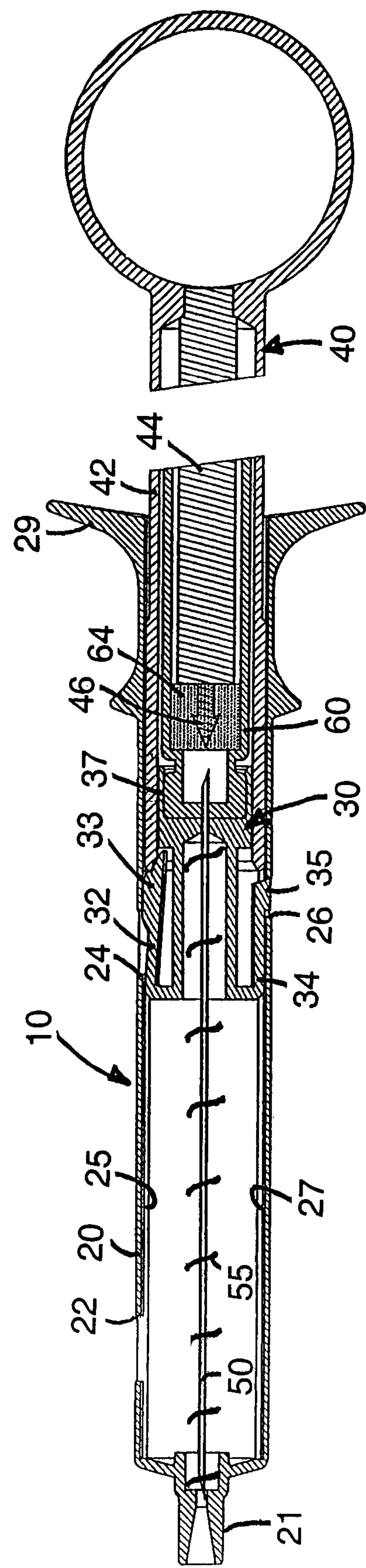
FIG. 3 is a cross-sectional view of the device illustrated in FIG. 1, illustrating the device in a position in which the needle is permanently retracted.
Figure 4:
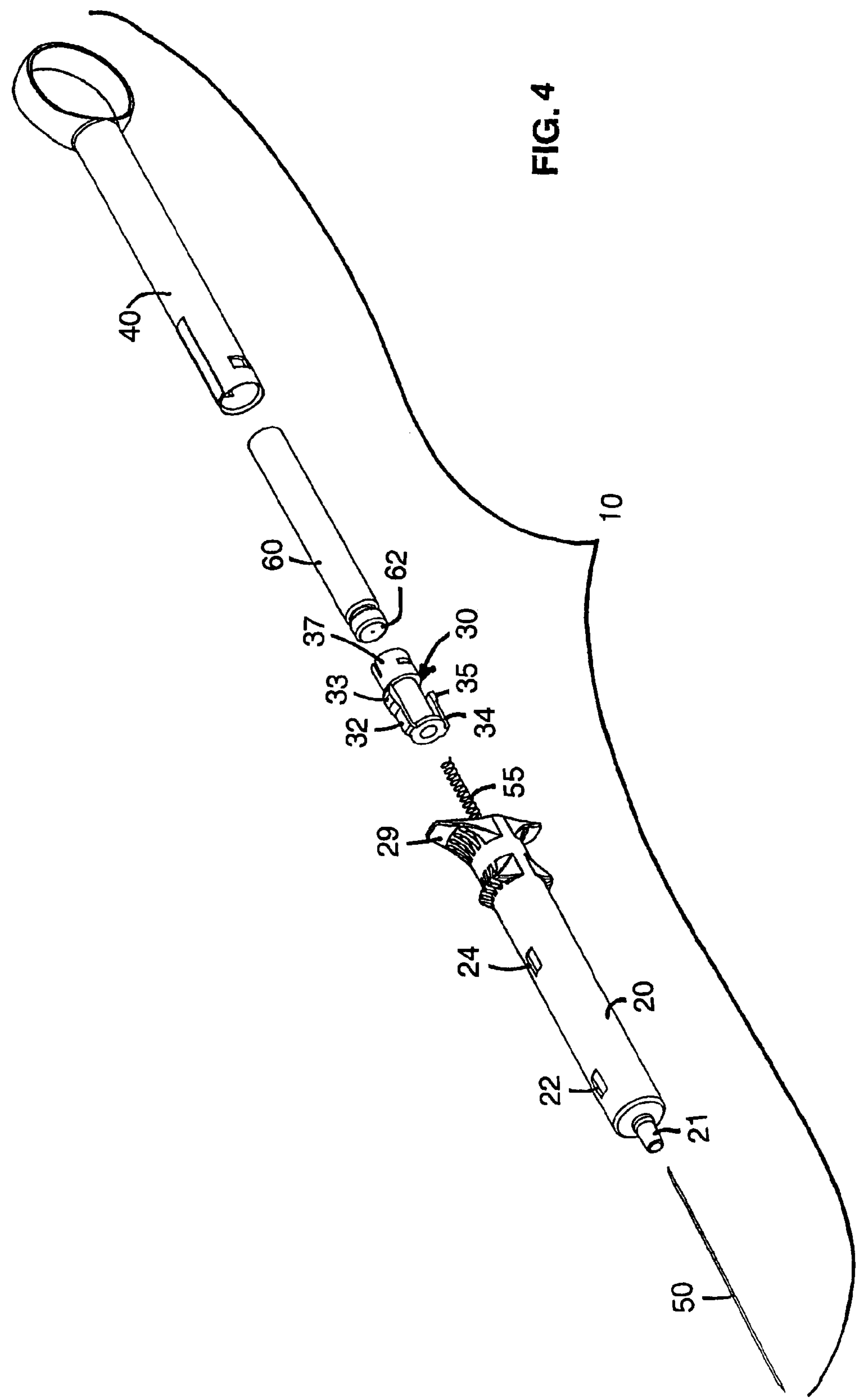
FIG. 4 is an exploded perspective view of the device illustrated in FIG. 1.

Referring now to FIGS. 1-10 in general, and FIG. 1 specifically, a medical device is designated generally 10. The device has a hollow housing 20 for receiving a cartridge that is pre-filled with medication. A needle 50 having a sharpened tip is provided for piercing the skin of a patient. A plunger 40 is operable to expel the medication from the cartridge 60 and into the patient through the needle 50. After an injection is administered, the needle can be temporarily retracted by depressing a button 33. A spring 55 then displaces the needle rearwardly so that the sharpened tip of the needle is enclosed within the housing 20. The needle is releasably retained and in a first retracted position by a first lock. The needle can be subsequently re-extended by moving the plunger 40 forwardly, which in turn displaces the needle 50 forwardly, until the button 33 reengages a forward lock. A subsequent injection can be administered to the patient by moving the plunger 40 further forwardly. In this way, a plurality of injections can be administered to the patient. After use, the needle can be primarily shielded by moving the plunger forwardly to displace all of the medication from the cartridge 60. The needle is then released and retracted to a second retracted position in which the needle is permanently locked in a retracted position to prevent further re-extension of the needle or further retraction of the needle, as illustrated in FIG. 3.

The details of the device 10 will now be described in greater detail. The housing 20 is a hollow generally cylindrical housing, preferably formed of plastic. The forward end of the housing 20 is generally closed having a nose 21 with a reduced diameter opening through which the needle 50 projects. The rearward end of the barrel 20 is generally open for receiving the cartridge 60 and the plunger 40. A plurality of flanges forming finger grips 29 are formed at the rearward end of the housing 20.

A forward locking aperture 22 is formed in the sidewall of the barrel 20. The forward locking aperture cooperates with the button 33 to releasably retain the needle 50 in the projecting position as described further below. A first rearward locking aperture 24, referred to as a releasable locking aperture, is formed in the sidewall of the barrel 20 rearward of and circumferentially aligned with the forward locking aperture 22. An axially elongated channel or slot 25 is formed in the interior of the barrel 20 between the forward locking aperture 22 and the releasable locking aperture 24. The channel cooperates with the button 33 to guide the button between the forward locking aperture 22 and the releasable locking aperture 24 as discussed further below. A second rearward locking aperture 26 referred to as a permanent locking aperture, is also formed in the sidewall of the barrel 20 intermediate the length of the barrel. The second locking aperture 26 is operable to permanently lock the needle 50 in a retracted position, as further described below.

A needle hub 30 is fixedly attached to the needle 50, and is axially displaceable within the interior of the housing 20. The needle hub 30 comprises an elongated hollow cylindrical central portion. The needle 50 extends through the hollow central portion of the hub and is bonded to the hub. The spring 55 circumscribes the needle 50 within the hollow central portion of the hub. The forward end of the spring bears against the forward end of the housing 20 and the rearward end of the spring bears against a wall formed at the rearward end of the needle hub 30. In this way, the spring 55 biases the needle and attached needle hub 30 rearwardly.

The needle hub 30 includes an axially elongated first arm 32 that is radially deformable. The button 33 is formed on the end of the first arm 32 remote from the central portion of the needle hub 30. Preferably the first arm 32 is formed so that the button 33 is biased radially outwardly into engagement with the housing 20. The button 33 has forward and rearward shoulders which engage the housing apertures 22, 24 to releasably lock the needle in forward and rearward position. Preferably, the rearward edge of the button 33 is tapered to cooperate with the plunger as discussed further below. The needle hub 30 further includes an axially elongated second arm 34 that is radially deformable. The second arm 34 is circumferentially spaced from the first arm 32, and preferably is disposed circumferentially approximately 180 degrees from the first arm. However, there may be additional arms for locking the needle if desired, and the circumferential spacing of the arms may be altered. A latch 35 is formed on the end of the second arm 34 remote from the central portion of the needle hub 30. Preferably, the second arm 34 is formed so that the latch 35 is biased radially outwardly into engagement with the housing 20. The latch 35 is operable to cooperate with the permanent rearward locking aperture 26 to fixedly lock the needle 50 in the retracted position.

The needle hub 30 further includes a cartridge lock 37 for attaching the cartridge 60 to the needle hub. The cartridge lock 37 comprises a socket sized to receive the head of the cartridge 60. The rearward end of the needle 50 forms a sharpened tip that projects into the socket. The rearward end of the cartridge lock 37 forms a flange projecting radially inwardly that cooperates with a circumferential groove formed on the head of the cartridge 60 to lock the cartridge onto the needle hub 30 to prevent relative displacement between the needle hub and the cartridge. Alternatively, the cartridge lock 37 can be formed without the retaining flange so that the cartridge 60 can be removed and replaced with a new cartridge. In this way, a plurality of cartridges can be used with the device 10 for the same patient, if desired.

The cartridge 60 is an elongated hollow cylinder forming a fluid reservoir. The cartridge 60 is filled with a premeasured amount of medicinal fluid. The forward end of the cartridge 60 is sealed by a pierceable septum 62. A circumferential groove is formed on the exterior of the cartridge 60 rearward of the septum 62. The rearward end of the cartridge 60 is sealed by a piston 64. The piston 64 forms a fluid-tight seal with the interior of the cartridge and is axially displaceable within the cartridge 60 to expel the medicine from the cartridge. The piston 64 includes a recess that cooperates with the plunger 40 as described further below. Further, preferably the frictional force between the piston 64 and the interior wall of the cartridge 60 is greater than biasing force of the spring 55.

The plunger 40 comprises a hollow plunger housing 42 and a plunger rod 44 disposed within the plunger housing. The plunger housing 42 is an elongated hollow cylinder having an open forward end. The plunger rod 44 is a solid cylindrical rod disposed coaxially within plunger housing 42. The plunger rod is sized so that an annular space is formed between the exterior of the plunger rod and the interior wall of the plunger housing 42. The thickness of this annular space is greater than the wall thickness of the cartridge 60. The forward end of the plunger rod 44 forms a connector 46 for attaching the plunger rod to the piston 64 of the cartridge 60. In the present instance the connector 46 is a barb, however the connector may be formed in other configurations such as threads configured to mate with corresponding threads that are optionally formed on the piston 64 in the cartridge 60.

Accordingly, configured as described above, the device 10 operates as follows. The cartridge 60 is inserted into the open end of the housing 20. The plunger 40 is inserted into the open rearward end of the housing 20 and the plunger is advanced to drive the cartridge forwardly until the head of the cartridge engages the cartridge lock 37. The sharpened rearward end of the needle pierces the septum 62 of the cartridge so that the needle is in fluid communication with the medicine in the cartridge. The sharpened forward tip of the needle 50 is then inserted into the patient. Displacing the plunger 40 forwardly drives the piston 64 forwardly injecting medicine into the patient through the needle. As the plunger is displaced forwardly, the plunger housing 42 telescopes over the cartridge, so that the wall of the cartridge is disposed between the plunger rod 44 and the plunger housing.

After a dose of medicine is injected into the patient, the needle can be retracted by depressing button 33, which displaces the button and arm 32 radially inwardly. The spring 55 then displaces the needle hub 30, the attached needle 50 and the plunger 40 rearwardly. As the spring 55 displaces the needle rearwardly, the button 33 rides in the upper slot 25, which aligns the button circumferentially. When the button 33 reaches the releasable locking aperture 24, the button deflects radially outwardly into engagement with the releasable locking aperture to releasably lock the needle 50 in a retracted position in which the forward sharpened tip of the needle is shielded within the device. If the medical professional desires to provide another injection into the same patient, the plunger is displaced forwardly which in turn displaces the needle hub 30 and needle 50 forwardly until the button 33 reengages the forward locking aperture 22, so that the needle is again releasably retained in a projecting position in which the forward sharpened tip of the needle is exposed for piercing the patient. After the needle hub 30 is locked in the forward position, continued advancement of the plunger operates to displace the piston 64 forwardly to inject further medicine into the patient. In this way, a plurality of injections can be administered to a patient, and the sharpened tip of the needle can be readily shielded after each injection.

After the medical professional is finished injecting medicine into the patient, the needle can be permanently retracted as follows. As shown in FIG. 2, the plunger 40 is displaced forwardly until all of the medicine is expelled from the cartridge. In this position, the forward edge of the plunger housing 42 engages the rearward edge of the button 33 displacing the button radially inwardly out of engagement with the forward locking aperture 22. The spring 55 then displaces the needle hub 30, plunger 40 and needle 50 rearwardly. Since the plunger housing 42 is in engagement with the button 33, the button does not displace radially outwardly into engagement with the releasable locking aperture 24. Instead, the needle hub 30 continues to be displaced rearwardly until the latch 35 reaches the permanent locking aperture 26. The latch 35 then displaces radially outwardly into engagement with the permanent locking aperture 26. The engagement between the latch 35 and locking aperture 26 substantially permanently impedes the needle hub, plunger and needle against forward or rearward axial displacement. The entire assembly can then be safely disposed.

Thus far, the present invention has been described as a device that can be used to administer a plurality of injections to a patient from a single cartridge. In some procedures, a patient may require a dosage of fluid that exceeds the capacity of one cartridge. As a result, it is desirable in some procedures to administer a plurality of injections from a plurality of cartridges using a single injection device.

Figure 5:
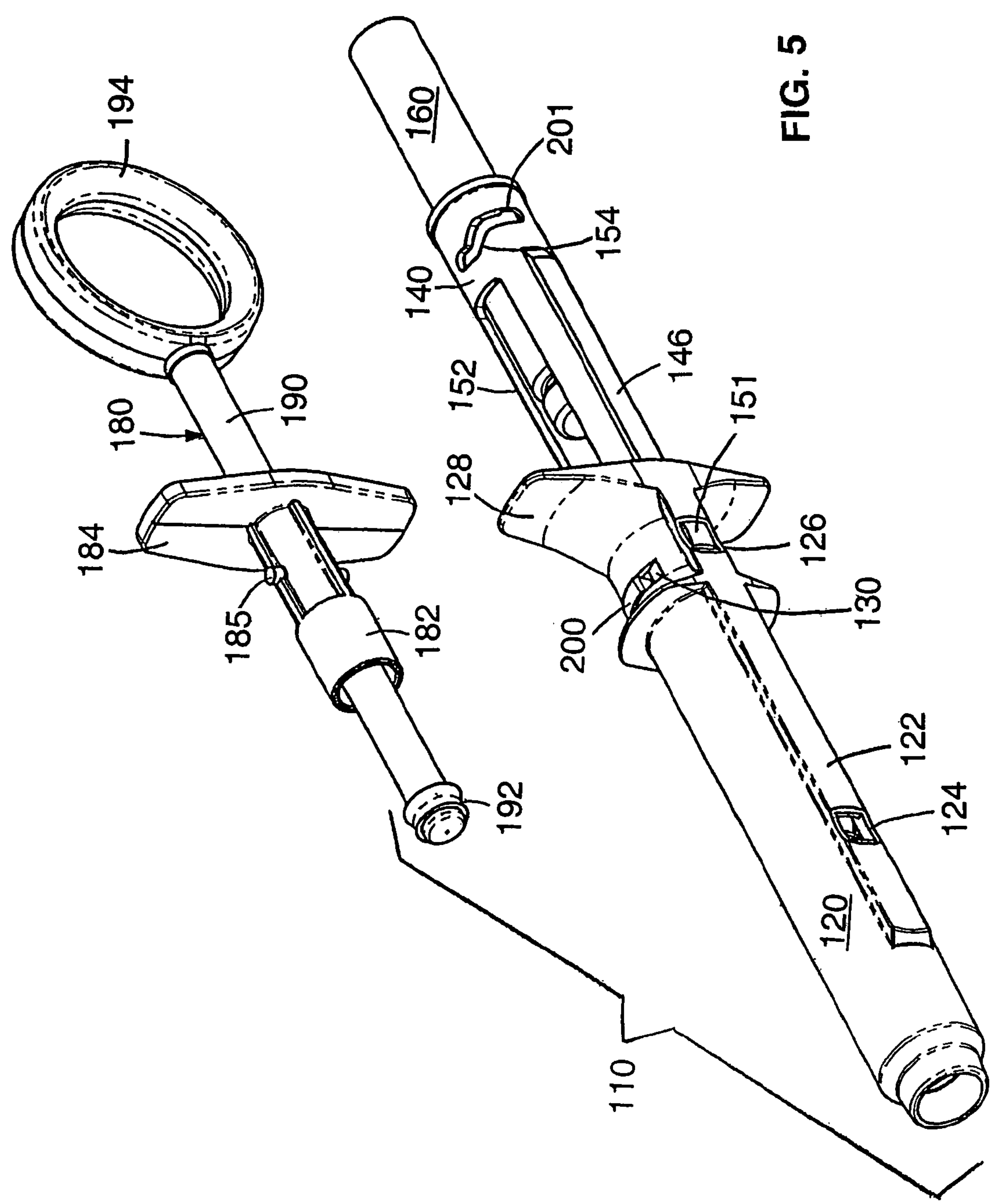
FIG. 5 is a perspective view of a second embodiment of the present invention, illustrating a retractable needle medical device with a plunger assembly detached.
Figure 6:
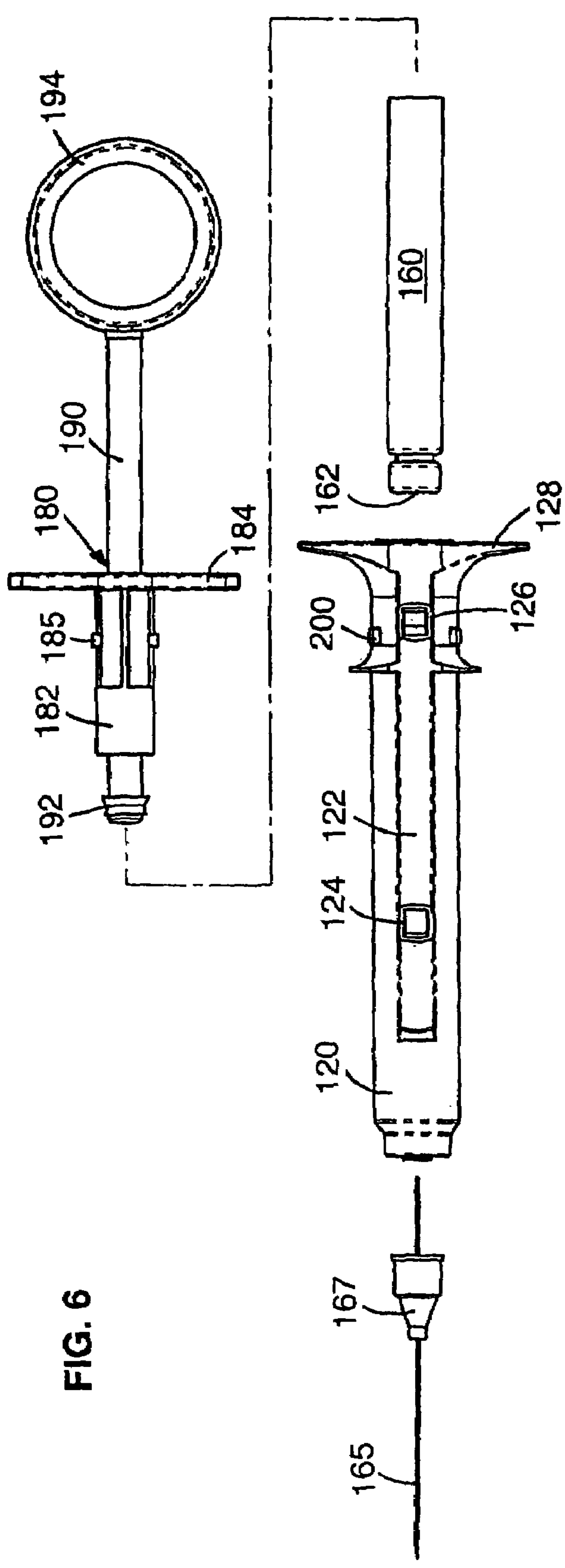
FIG. 6 is an exploded side view of the medical device illustrated in FIG. 5.

Referring now to FIGS. 5 and 6, a second embodiment of the present invention is shown and designated 110. The device 110 includes a needle 165 for piercing a patient, and a plunger assembly 180 for ejecting medication from a pre-filled cartridge 160 into a patient. At the end of an injection, the needle 165 can be automatically shielded to prevent inadvertent contact with the contaminated needle. Subsequently, the needle can be re-extended to provide a further injection to the patient. In this way, a plurality of injections can be given to a patient while allowing the needle to be safely shielded between injections.

Figure 7:
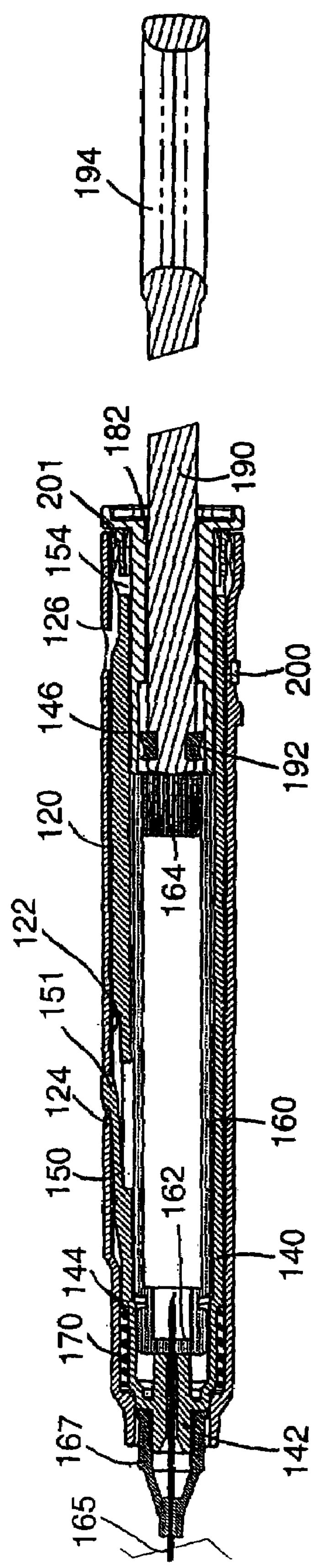
FIG. 7 is a cross-sectional view of the medical device illustrated in FIG. 6 illustrating the device prior to injection.

The device includes a generally cylindrical barrel 120 and an inner housing 140 that is displaceable within the barrel 120. The inner housing 140 is generally hollow, having a socket for receiving the cartridge 160. The needle 165 is attached to the forward end of the inner housing 140, as shown in FIG. 7. A plunger assembly 180 attached to the rearward end of the inner housing 140 is operable to expel the medicine from the cartridge.

Figure 9:
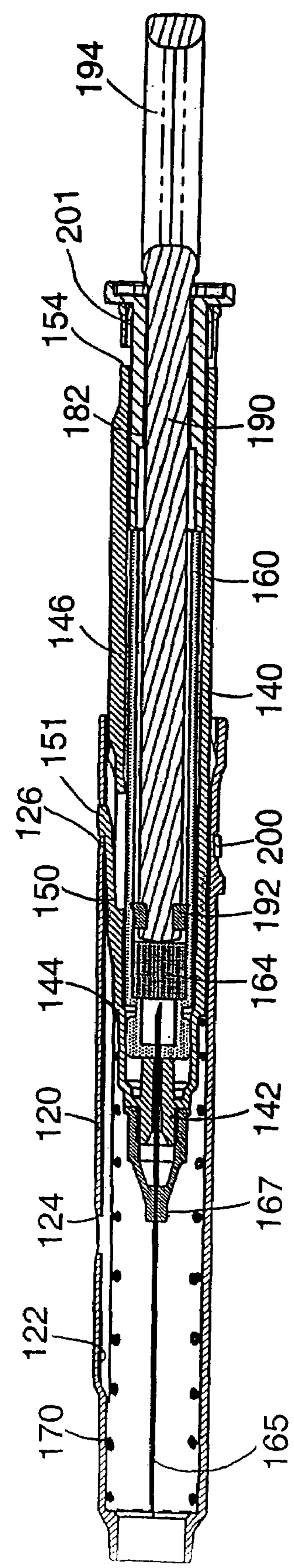
FIG. 9 is a cross-sectional view of the medical device illustrated in FIG. 7, illustrating the device in a retracted position.

A compression spring 170 is disposed between the barrel 120 and the inner housing 140. The spring 170 biases the inner housing 140 rearwardly toward a retracted position in which the needle 165 is shielded within the barrel as shown in FIG. 9. A latch 150 attached to the inner housing 140 engages the barrel 120 to releasably retain the inner housing against the bias of the spring, as shown in FIG. 7.

Figure 8:
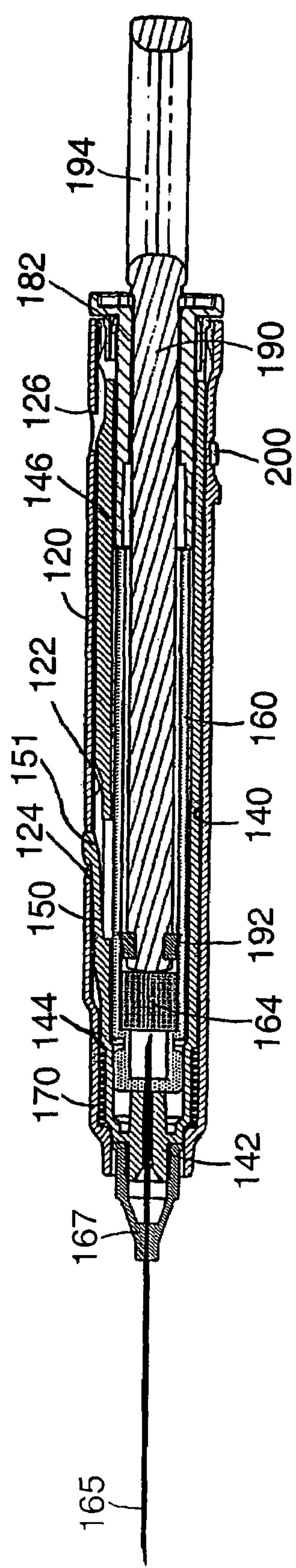
FIG. 8 is a cross-sectional view of the medical device illustrated in FIG. 7, illustrating the device at the end of an injection.

The latch 150 includes a manually actuable button 151. By depressing the button 151, the latch 150 disengages the barrel 120 so that the inner housing 140 and attached needle 165 can be retracted. In the retracted position the latch 150 re-engages the barrel 120, as shown in a FIG. 9. By depressing the button 151 and pushing the plunger assembly 180 forwardly, the inner housing 140 and attached needle 165 can be re-extended until the latch 150 re-engages the barrel in the forward position, as shown in FIG. 8.

Referring now to FIGS. 5-7, the details of the injector 110 will be described in greater detail. The outer barrel 120 is generally cylindrical, having an open forward end and an open rearward end. An annular shoulder formed in the interior of the barrel adjacent the open front end provides a surface that the spring 170 bears against. The barrel 120 comprises a pair of opposing finger grips 128 projecting radially outwardly from the rearward end of the barrel. The finger grips provide a manual surface for grasping the barrel during use.

An axially elongated recess or channel 122 is formed in the barrel such that the channel protrudes radially outwardly from the side of the barrel, as shown in FIGS. 5 and 7. The channel 122 preferably extends substantially the length of the barrel 120 from the rearward end of the barrel, terminating short of the forward end of the barrel. The channel 122 provides a clearance space for the latch 150 during axial displacement of the inner housing 140 relative to the barrel 120. In addition, the channel 122 cooperates with an elongated alignment rib 146 formed on the inner housing 140 to prevent rotation of the inner housing relative to the barrel 120.

The barrel 120 includes a pair of locking windows 124, 126 that cooperate with the latch 150 of the inner housing to releasably latch the inner housing 140 to the barrel 120. The locking windows 124, 126 are axially aligned and spaced apart from one another, as shown in FIG. 6. Preferably, the locking windows 124, 126 are disposed along the length of the channel 122. The latch 150 on the inner housing 140 cooperates with the front window 124 to releasably lock the inner housing in a forward position, and the latch cooperates with the rear window 126 to releasably lock the inner housing in a retracted position.

Referring to FIG. 5, a pair of lateral slots 130 are formed in the wall of the barrel 120 transverse the axis of the barrel, adjacent the rearward end of the barrel. Preferably the slots 130 are formed approximately 180 degrees apart from one another to provide a top slot and a bottom slot through the wall of the barrel. The slots 130 cooperate with a locking clip 200 to prevent the inner housing 140 from being completely removed from the barrel 120, as discussed further below.

Referring now to FIGS. 5 and 7, the inner housing 140 comprises an elongated hollow cylinder. The front end of the inner housing is generally closed, having a nose 142 that cooperates with a needle hub 167 to attach the needle to the inner housing. Specifically, the needle 165 is fixedly attached to a needle hub 167 having a generally open rearward end forming a female connector. As shown in FIGS. 6 and 7, the needle hub 167 is mounted on the needle 165 along the length of the needle so that the forward sharpened tip of the needle projects forwardly from the needle hub and the sharpened rearward end of the needle projects rearwardly from the needle hub. As shown in FIG. 7, the nose 142 of the inner housing 140 forms a male connector that cooperates with the interior of the needle hub 167 to form a fluid-tight connection between the needle, and the inner housing. The nose 142 has a reduced diameter opening through which the rearward end of the needle 165 extends, and the length of the needle 165 projecting rearwardly from the needle hub 167 is sufficiently long to ensure that the rearward sharpened end of the needle projects into the interior of the inner housing 140 to enable the needle to pierce the septum 162 of the cartridge 160.

A circumferential shoulder 144 is formed on the exterior of the inner housing 140, adjacent the nose 142. The shoulder 144 provides a surface against which the rearward end of the spring 170 bears. In this way, an annular spring housing is formed in the radial space between the outer surface of the inner housing and the inner surface of the barrel 120, extending between the annular shoulder formed at the front and of the barrel end the circumferential shoulder 144 formed on the inner housing.

As shown in FIG. 7, the latch 150 is integrally formed in the side of the inner housing 140. The latch 150 is an axially elongated radially deformable arm biased radially outwardly toward the barrel 120. Preferably, the latch 150 has a width that is slightly less than the width of the channel 122 formed in the side of the barrel 120, so that the latch can slide freely through the channel during retraction and re-extension of the needle, as discussed further below.

A button 151 or locking tab is formed on the terminal end of the latch 150 remote from the inner housing. As shown in FIG. 7, the button 151 engages the front locking window 124 to releasably lock the inner housing against axial displacement relative to the barrel 120. Similarly, the button 151 engages the rear locking window 126 to releasably lock the inner housing against axial displacement relative to the barrel 120. A cut-out in the inner housing 140 adjacent the latch 150 provides a clearance space to allow the latch to be displaced radially inwardly out of engagement with the barrel.

Figure 10:
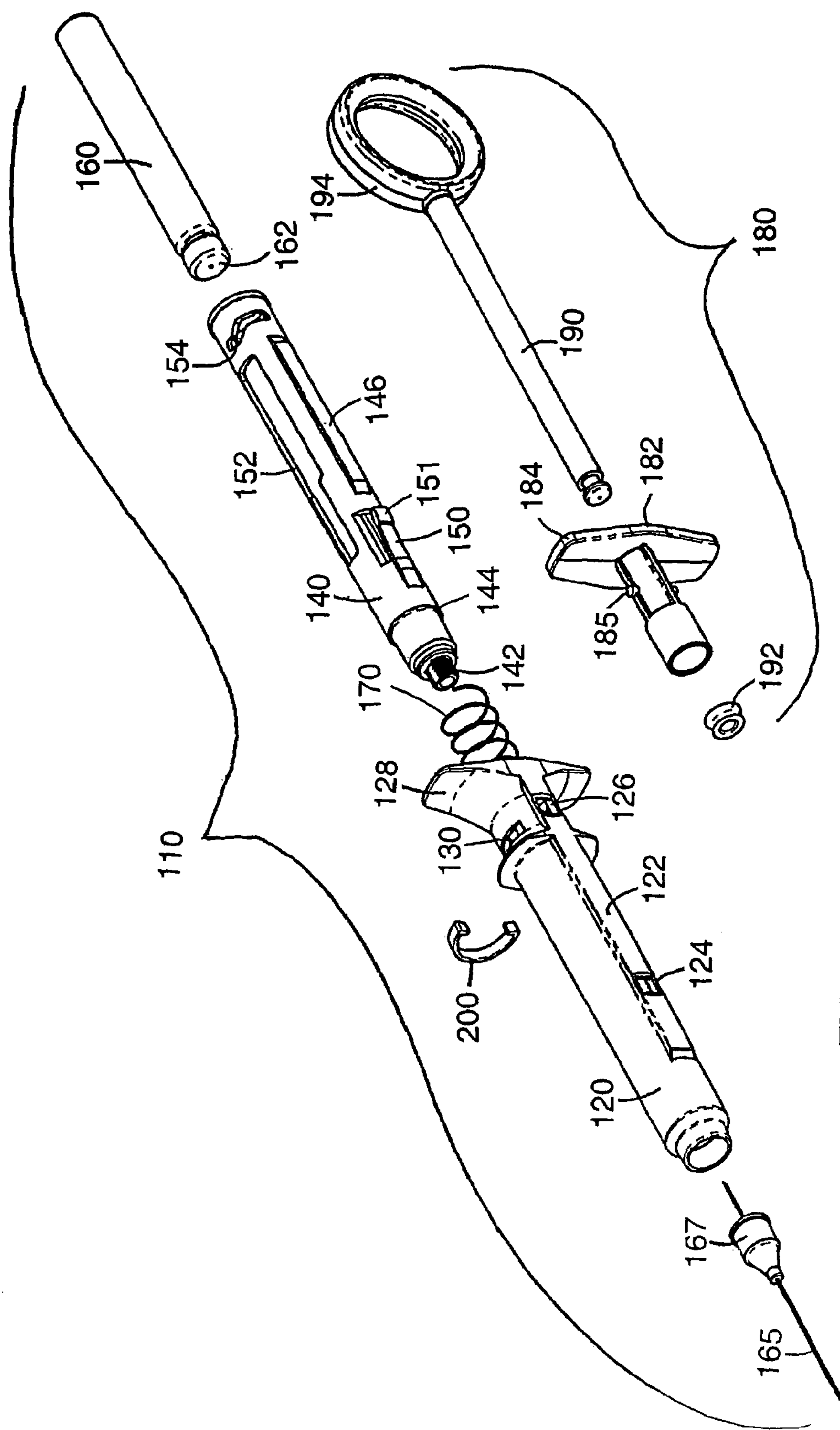
FIG. 10 is an exploded perspective view of the medical device illustrated in FIG. 5.
Figure 11:
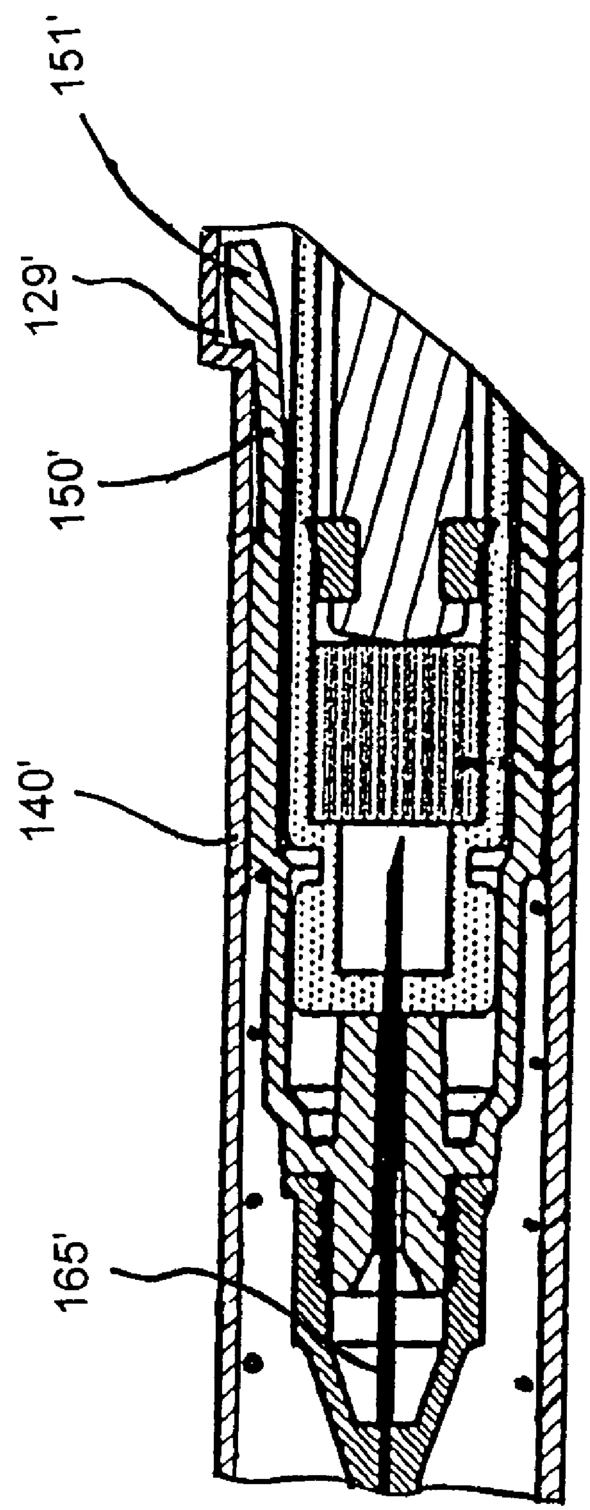
FIG. 11 is a cross-sectional view of another embodiment of the medical device.

Preferably, an axially elongated alignment rib 146 is formed on the exterior of the inner housing 140. As shown in FIG. 10, preferably the rib 146 is axially aligned with the latch 150. Referring again to FIG. 7, the rib 146 projects radially outwardly from the inner housing 140 into engagement with the channel 122 in the barrel 120. Preferably, the rib 146 has a width that is slightly less than the width of the channel 122 formed in the side of the barrel 120. In this way, the rib 146 forms a sliding engagement with the channel 122, allowing the inner housing 140 to slide freely axially relative to the barrel.

The engagement between the rib 146 and channel 122 operates similar to a key and keyway to prevent rotation of the inner housing relative to the barrel. In addition, the rib 146 also operates to support torque applied to the inner housing, which might otherwise be transferred to the latch 150, which could potentially fracture the latch. Such torque may be applied when the needle is screwed into the device, or when the plunger assembly is twisted to engage the housing.

As shown in FIGS. 5 and 10, a pair of locking slots 154 are formed adjacent the rearward end of the inner housing. Preferably, the locking slots are modified Z-shaped slots that cooperate with locking pins 185 on the plunger assembly 180 to attach the plunger assembly to the inner housing.

The rearward end of the inner housing 140 is open, having an inner diameter that is greater than the outer diameter of the cartridge 160. In this way, the cartridge 160 can be inserted into the rearward end of the inner housing to mount the cartridge within the housing. The cartridge 160 is inserted into the inner housing until the forward end of the cartridge abuts the forward end of the inner housing so that the needle 165 pierces the cartridge, as shown in FIG. 7.

As in the first embodiment, the cartridge 160 is an elongated hollow cylinder forming a fluid reservoir. The cartridge is filled with a pre-measured amount of medicinal fluid. The forward end of the cartridge 160 is sealed by a pierceable septum 162. A circumferential groove is formed on the exterior of the cartridge 160 rearward of the septum 162. The rearward end of the cartridge 160 is sealed by a piston 164 that forms a fluid-tight seal with the interior of the cartridge. The piston is axially displaceable within the cartridge to expel medicine from the cartridge.

Referring to FIGS. 5, 6 and 10, the details of the plunger assembly 180 will now be described. The plunger assembly 180 is operable to expel the medicine from the cartridge 160 during an injection. The plunger assembly 180 may be designed either as a single-use element or as a reusable element. Specifically, the plunger assembly 180 may be formed of an inexpensive readily formable material such as plastic, and permanently attached to the inner housing 140 so that the plunger assembly is discarded along with the device after use. Alternatively, the plunger assembly 180 may be formed of a durable material that can be sterilized after use. For instance, the plunger assembly may be formed of a material such as nickel-plated metal or stainless-steel that can be sterilized by an autoclave after use. If the plunger assembly is intended for reuse, the connection between the plunger assembly and the inner housing is releasable, so that the barrel 120, inner housing 140 and needle 165 can be detached and safely disposed of after use.

The plunger assembly 180 includes an elongated plunger rod 190 that is axially displaceable within the plunger sleeve 182. Preferably, a loop 194 is formed on the rear end of the plunger rod 190, forming an opening for the user's thumb to manipulate the plunger rod during use. The loop 194 and the finger grips in front of flanges 128 allow the operator to aspirate the device with one hand. In addition, preferably a circumferential groove is formed in the plunger rod 190 adjacent the front end of the plunger rod, as shown in FIG. 10. The groove provides a seat for receiving a plunger seal 192 as shown in FIG. 7.

The plunger sleeve 182 is a generally hollow cylindrical sleeve having an internal bore for receiving the plunger rod 190. A pair of finger grips 184 project radially outwardly from the rearward end of the plunger sleeve 182, providing a surface for engaging the sleeve to drive the entire plunger assembly forwardly during re-extension of the needle 165, as described below. The bore of the plunger sleeve 182 is enlarged adjacent the forward end of the sleeve so that the plunger seal 192 can be received within the forward end of the sleeve, as shown in FIG. 7. The plunger seal 192 preferably forms a fluid-tight seal with the inner wall of the cartridge.

Referring to FIGS. 5 and 10, a pair of locking pins 185 project radially outwardly from the plunger sleeve 182. Preferably, the locking pins are circumferentially spaced apart from one another approximately 180 degrees. A pair of internal channels 201 are disposed in the interior of inner housing 140 adjacent to receive locking pins 185 on plunger assembly 180 and guide the locking pins into the Z-shaped locking slots 154 as the plunger assembly is inserted into the inner housing. The locking pins 185 snap into recesses at the end of the slots to releasably connect the plunger assembly 180 to the inner housing 140.

The plunger assembly 180 is attached to the inner housing 140 as follows. After a cartridge 160 is inserted into the inner housing 140, the plunger rod 190 is withdrawn so that the front end of the plunger rod is disposed within the bore of the plunger sleeve 182, as shown in FIG. 7. The plunger assembly is inserted into the rearward end of the inner housing 140 with the locking pins 185 axially aligned with interior channels 201. The plunger assembly 180 is then advanced toward the front of the inner housing 140 until locking pins 185 enter locking slots 154. Preferably, the axial distance between the locking pins 185 and the finger grips 184 is substantially similar to the axial distance between the rearward edge of the inner housing 140 and the locking slots 154. In this way, the locking pins 185 can be readily aligned with the locking slots 154 by inserting the plunger sleeve 182 into the inner housing 140 until the finger grips 184 engage the rearward end of the inner housing.

With reference to FIG. 5, the plunger assembly 180 is rotated approximately 90 degrees relative to the view in FIG. 5 when the plunger assembly is inserted into the inner housing 140. After the locking pins 185 pass through interior channels 201 and enter locking slots 154, the plunger sleeve 182 is rotated approximately 90 degrees to lock the plunger assembly to the inner housing. This rotated orientation is reflected in the illustration in FIG. 5.

As described above, the inner housing 140 is axially displaceable relative to the barrel 120. Since the needle 165 is attached to the inner housing 140, the contaminated needle will be exposed if the inner housing is removed from the barrel after use. Accordingly, as mentioned previously, preferably the device 110 includes an element for preventing the inner housing 140 from being completely removed from the barrel 120. Specifically, preferably the device includes a locking clip 200 that provides a stop limiting the rearward displacement of the inner housing.

As shown in FIG. 10, the locking clip 200 is a generally C-shaped clip. The ends of the clip terminate in hooks that project radially inwardly. The locking clip 200 snaps onto the barrel 120 so that the terminal ends of the locking clip project radially inwardly through the side slots 130 adjacent the rearward end of the barrel. Preferably, the locking clip is attached to the barrel during manufacturing after the inner housing 140 and spring 170 are inserted into the barrel 120.

As shown in FIG. 10, a pair of opposing axially elongated access windows 152 are formed in the inner housing circumferentially spaced from the alignment rib 146. The forward end of the access windows 152 form shoulders that engage the ends of the locking clip 200 that extend into the barrel. In this way, the engagement between the locking clip 200 and the forward end of the access windows 152 limits the rearward displacement of the inner housing 140 relative to the barrel 120, thereby preventing the inner housing from being completely removed from the barrel, which would expose the contaminated needle 165.

The operation of the device will now be described. A cartridge 160 is inserted into the inner housing 140. The plunger assembly 180 is then inserted into the inner housing 140 and advanced forwardly until the locking pins 185 register with the locking slots 154 on the inner housing. The plunger sleeve 182 is then rotated so that the locking pins 185 follow the locking slots 154 until the plunger assembly is attached to the inner housing. The needle hub 167 is then attached to the forward end of the inner housing so that the rearward end of the needle 165 pierces the septum 162 on the cartridge. The septum 162 then forms a seal around the needle 165 to prevent medicine from leaking out of the cartridge 160 around the needle. Preferably, prior to attaching the plunger assembly 180 to the inner housing 140, the plunger rod 190 is displaced so that the front end of the plunger rod is disposed within the bore of the plunger sleeve 182 adjacent the front end of the plunger sleeve as shown in FIG. 7.

FIG. 7 illustrates the device 110 as it appears after the plunger assembly 180 is attached to the inner housing 140 and prior to an injection. The needle 165 is inserted into a patient. It may be desirable to check to see whether the needle pierced a blood vessel in the patient. This can be done by pulling the plunger rod 190 rearwardly. Prior to piercing the patient, the plunger rod 190 may be advanced into the cartridge a short distance until the plunger seal 192 enters the cartridge. Since the plunger seal 192 forms a fluid-tight seal with the interior of the cartridge 160, pulling rearwardly on the plunger rod forms a vacuum that displaces the cartridge piston 164 rearwardly. If the needle pierced a blood vessel in the patient, a flash of blood will enter the cartridge when the piston 164 is displaced rearwardly. Preferably the cartridge, inner housing and barrel are formed of translucent or transparent materials so that the flash of blood is visible. If blood is detected, an alternate injection can be located.

Once the needle 165 is properly inserted into the patient, the plunger rod 190 is advanced, thereby advancing the piston 164 to expel medication from the cartridge into the patient through the needle 165. To do so, the user grasps the finger grips 128 on the barrel 120 between two fingers and inserts a thumb into the loop 194, and squeezes the thumb and fingers together.

In many applications, it is desirable to inject the medication using a series of small injections. In such applications, less than the entire amount of the medication in the cartridge is injected during a single injection. After each injection, the needle 165 can be retracted to shield the needle to prevent inadvertent contact with the contaminated needle between injections.

The needle 165 is retracted as follows. The user pushes the button 151 downwardly out of engagement with the front locking window 124. The inner housing 140 is then free to be displaced rearwardly under the bias of the spring 170. However, the needle will not retract until the user releases the plunger, which is also displaced rearwardly during retraction. Alternatively, the user ban release the finger grips 128 on the barrel 120, allowing the barrel 120 to be displaced forwardly to shield the needle. Either way, the button should be pushed while the plunger or barrel is released. Otherwise, the button may re-engage the front locking window before it is released.

As the inner housing 140 is displaced rearwardly relative to the barrel 120, the latch 150 is compressed radially inwardly, engaging the channel 122. In addition, during retraction, the alignment rib 146 and the button 151 ride within the channel 122, maintaining the alignment between the button and the locking windows 124, 126. At the end of retraction, the button 151 is aligned with the rear locking window 126, and the latch 150 resiliently deflects outwardly so that the button engages the rear locking window, as shown in FIG. 9. In this position, the contaminated sharpened tip of the needle is shielded within the barrel 120.

Further injections can be administered by re-extending the needle 165. This is done by pressing the button 151 downwardly out of engagement with the rear locking window 126 and simultaneously pushing the plunger assembly 180 forwardly until the button 151 is aligned with the front locking window 126. The latch 150 then resiliently deflects outwardly so that the button engages the front locking window 124. If the inner housing is advanced by pushing forward on the plunger rod, the force may also advance the piston 164, which would inadvertently expel medication from the cartridge. Accordingly, preferably the plunger assembly is advanced by grasping the finger grips 128 on the barrel and the finger grips 184 on the plunger assembly. The needle can then be re-extended without expelling medicine by pushing forward on the finger grips 184 attached to the plunger assembly.

If all of the medication is expelled from the cartridge, and further injections are desired, the empty cartridge can be replaced with a new cartridge. To do so, the needle 165 is retracted, as shown in FIG. 9, so that the inner housing 140 projects rearwardly from the barrel 120. The plunger rod 190 is then pulled rearwardly out of the cartridge 160 and into the bore of the plunger sleeve 182. Referring to FIG. 5, when the inner housing is retracted, the access windows 152 in the inner housing provide access to the cartridge. Specifically, the access windows 152 are wide enough to allow the user to grasp the cartridge to pull the cartridge out the rearward end of the inner housing. Accordingly, the cartridge is manually grasped through the access windows 152, pulled rearwardly out of engagement with the rearward end of the needle 165, and out the rearward end of the inner housing 140. A new cartridge can then be inserted through the rearward end of the inner housing and advanced until the reward end of the needle pierces the septum on the cartridge. The inner housing 140 can then be re-extended as described previously to administer further injections of medicine. In this way, a plurality of injections can be administered from a plurality of cartridges using a single device, while shielding the contaminated needle between injections.

It may be desirable to further include another lock for permanently locking the needle 165 in the retracted position after use. For instance, the barrel may include a locking recess adjacent the rearward end of the barrel, circumferentially spaced from the rear locking window 126. After the final injection is administered, the inner housing 140 is retracted rearwardly until the latch 150 engages the rear locking window 126. To permanently lock the inner housing, the button 151 is then pushed inwardly and the inner housing is rotated relative to the outer housing until the latch 150 engages the locking recess. To facilitate this twisting at the end of retraction, it may be necessary to modify the alignment rib 146 to allow the inner housing to rotate relative to the barrel after retraction.

The terms and expressions which have been employed are used as terms of description and not of limitation. There is no intention in the use of such terms and expressions of excluding any equivalents of the features shown and described or portions thereof. It is recognized, however that various modifications are possible within the scope and spirit of the invention as set forth in the following claims.

What is claimed is:

1. A method for injecting medication, the method comprising:

providing a medical device that includes a displaceable housing and a barrel, wherein the housing is connected to a needle that defines a sharpened tip;

piercing a patient with the needle; injecting fluid into the patient;

retracting the needle so that the sharpened tip is shielded against inadvertent contact;

releasably locking the needle in the retracted position;

re-extending the needle to the extended position by displacing the housing relative to the barrel while substantially preventing rotation of the housing relative to the barrel such that the needle moves from the extended position to the retracted position and back to the extended position again substantially without rotation of the housing relative to the barrel;

piercing the patient a subsequent time with the needle;

retracting the needle a subsequent time so that the sharpened tip is shielded against inadvertent contact; and permanently locking the needle in a retracted position to prevent further axial displacement of the needle after the needle is retracted the subsequent time.

2. The method of claim 1, further comprising providing a biasing element for displacing the needle rearwardly during retraction of the needle.

3. The method of claim 1, further comprising providing a pre-filled cartridge, wherein injecting fluid into the patient comprises injecting fluid from the cartridge.

4. The method of claim 1, further comprising providing a lock for releasably retaining the needle in a projecting position in which the sharpened tip of the needle is exposed for use.

5. A medical device, comprising:

a hollow housing having an open rearward end for receiving a cartridge containing fluid, wherein the housing is slidably displaceable within a barrel;

a needle having a sharpened tip in fluid communication with the cartridge;

a first lock configured to retain the housing such that the needle is in a projecting position in which the sharpened tip of the needle is exposed for use, wherein the first lock is configured to release the housing due to radial deformation of an actuator substantially without the housing rotating relative to the barrel;

a second lock configured to releasably retain the needle in a first retracted position in which the sharpened tip of the needle is shielded against inadvertent contact;

a third lock configured to permanently retain the needle in a second retracted position in which the sharpened tip of the needle is shielded against inadvertent contact, wherein the lock permanently impedes axial displacement of the needle; and a biasing element biasing the needle rearwardly.

6. The medical device of claim 5, further comprising a manually operable actuator for releasing the first lock to permit retraction of the needle toward the second lock.

7. The medical device of claim 6, wherein the manually operable actuator is configured to release the second lock to permit retraction of the needle toward the third lock.

8. A method for injecting medical fluid, the method comprising:

providing a medical device that includes a displaceable housing and a barrel, wherein the housing is connected to a needle that defines a sharpened tip;

piercing a patient with the needle in an extended position;

injecting fluid from a first cartridge into the patient;

retracting the needle into the barrel by displacing the housing relative to the barrel while substantially preventing rotation of the housing relative to the barrel, wherein the sharpened tip is shielded against inadvertent contact when the tip is within the barrel;

releasably locking the needle in a retracted position within the barrel;

replacing the first cartridge with a second cartridge containing fluid;

re-extending the needle to the extended position by displacing the housing relative to the barrel while substantially preventing rotation of the housing relative to the barrel such that the needle moves from the extended position to the retracted position and back to the extended position again substantially without rotation of the housing relative to the barrel;

injecting fluid from the second cartridge into the patient; and retracting the needle into the barrel a subsequent time by displacing the housing while substantially preventing rotation of the housing relative to the barrel.

9. The method of claim 8, further comprising providing a biasing element for displacing the needle rearwardly during retraction of the needle.

10. The method of claim 8, further comprising permanently locking the needle in a retracted position to prevent further axial displacement of the needle after the needle is retracted the subsequent time.

11. The method of claim 8, further comprising releasably locking the needle in a projection position in which the sharpened tip of the needle is exposed for use.

12. A medical device comprising:

a hollow barrel;

an inner housing slidably displaceable within the barrel, and having an opening for receiving a cartridge;

a needle connected to the housing and having a sharpened tip configured to fluidly communicate with the cartridge;

a plunger operable to expel fluid from the cartridge;

a first lock configured to retain the housing such that the needle is in a projecting position in which the sharpened tip of the needle is exposed for use, wherein the first lock is configured to release the housing due to radial deformation of an actuator substantially without the housing rotating relative to the barrel;

a second lock configured to releasably retain the needle in a retracted position in which the sharpened tip of the needle is shielded against inadvertent contact;

a guide configured to substantially prevent rotation of the housing relative to the barrel as the housing moves from the first lock to the second lock and configured to substantially prevent rotation of the housing relative to the barrel as the housing moves from the second lock to the first lock; and a biasing element biasing the needle rearwardly.

13. The medical device of claim 12, wherein the actuator is manually operable.

14. The medical device of claim 12, further comprising a third lock configured to permanently impede axial displacement of the housing and thereby retain the needle in a retracted position in which the sharpened tip of the needle is shielded against inadvertent contact.

15. The medical device of claim 12, wherein the plunger is connected to the inner housing.

16. The medical device of claim 12, wherein the second lock is configured to release the housing due to radial deformation of the actuator substantially without the housing rotating relative to the barrel.

17. The medical device of claim 12, wherein the guide comprises a groove on one of the barrel and the housing and a follower on the other of the barrel and the housing that is co-operable with the groove.

18. The medical device of claim 12, wherein the first lock comprises a latch connected to one of the barrel and the housing and further comprises an opening in the other of the barrel and the housing, wherein the opening is configured to cooperate with the latch to selectively impede axial displacement of the housing to retain the needle in the projecting position.

19. The medical device of claim 12, wherein the plunger is connected to one of the barrel and the housing, and wherein the cartridge can be removed and replaced with another cartridge without detaching the plunger.

* * * * *